United States Patent [19]
Hamparian et al.

[11] Patent Number: 6,012,034
[45] Date of Patent: Jan. 4, 2000

[54] SYSTEM AND METHOD FOR SELECTING AN INTRAVENOUS DEVICE

[75] Inventors: Beth Giles Hamparian, Streamwood; Ronald L. Randle, Wheaton; James A. Meurer, Naperville, all of Ill.; Felipe Velasquez, North Bergen, N.J.; Fred Dufresne, Sharon, Mass.

[73] Assignee: Becton, Dickinson and Company, Franklin Lakes, N.J.

[21] Appl. No.: 08/910,555

[22] Filed: Aug. 18, 1997

[51] Int. Cl.[7] .................................................. G06F 17/60
[52] U.S. Cl. .................................. 705/2; 705/1; 706/47; 604/95
[58] Field of Search .......................... 705/2, 3, 1; 706/47; 604/95

[56] References Cited

U.S. PATENT DOCUMENTS

| | | | |
|---|---|---|---|
| 4,464,172 | 8/1984 | Lichtenstein | 604/65 |
| 4,634,426 | 1/1987 | Kamen | 604/65 |
| 4,839,822 | 6/1989 | Dormond et al. | 364/513 |
| 5,041,086 | 8/1991 | Koenig et al. | 604/65 |
| 5,088,981 | 2/1992 | Howson et al. | 604/31 |
| 5,306,250 | 4/1994 | March et al. | 604/104 |
| 5,317,506 | 5/1994 | Coutré et al. | 364/413.02 |
| 5,397,307 | 3/1995 | Goodin | 604/96 |
| 5,523,092 | 6/1996 | Hanson et al. | 424/423 |
| 5,560,352 | 10/1996 | Heim et al. | 128/203.12 |
| 5,572,421 | 11/1996 | Altman et al. | 705/3 |
| 5,583,758 | 12/1996 | McIlroy et al. | 705/2 |
| 5,606,976 | 3/1997 | Marshall et al. | 128/671 |
| 5,607,460 | 3/1997 | Kroll et al. | 607/30 |
| 5,609,575 | 3/1997 | Larson et al. | 604/65 |
| 5,610,811 | 3/1997 | Honda | 705/2 |
| 5,758,031 | 5/1998 | DeSilva | 706/47 |
| 5,758,096 | 5/1998 | Barsky et al. | 705/3 |
| 5,819,229 | 10/1998 | Boppe | 705/2 |

OTHER PUBLICATIONS

Bagnall–Reeb, H.A., et al. "Management of Cutaneous Reactions and Mechanical Complications of Central Venous Access Devices in Pediatric Patients With Cancer: Algorithms for Decision Making", *Oncology Nursing Forum*. vol. 17, No. 5 (1990), pp. 677–681.

Baranowski, L. "Central Venous Access Devices: Current Technologies, Uses and Management Strategies", *Journal of Intravenous Nursing*. vol. 16, No. 3 (May/Jun., 1993), pp. 167–194.

Barvais, L., et al. "CIN: Software Designed to Compute the Infusion Delivery of Intravenous Anesthetic Drugs on a Personal Computer", *Journal of Clinical Monitoring*. vol. 4, No. 2 (Apr., 1988), pp. 128–130.

Camp–Sorrell, et al. "Teaching Oncology Nurses About Epidural Catheters", *Oncology Nursing Forum*, vol. 17, No. 5 (1990), pp. 683–689.

Cantraine, F. "Computer Driven I.V. Injection Systems", *Acta Anaesthesiologica Belgica*. (1988), 39, pp. 257–266.

Kastner, J.K. "Treatment Selection and Explanation in Expert Medical Consultation: Application to a Model of Ocular Herpes Simplex", Department of Computer Science: Rutgers University. (Sep., 1982).

(List continued on next page.)

*Primary Examiner*—Emanuel Todd Voeltz
*Assistant Examiner*—George D. Morgan
*Attorney, Agent, or Firm*—Eric M. Lee

[57] ABSTRACT

A computer system comprising a control program stored in a memory recommends an intravenous device for infusion therapy based on input entered by a user. The control program includes an execution program for interacting with the user to elicit responses and to provide output to the user. The user inputs parameters to the prompts of the execution program to provide the control program with information regarding the infusion and the patient. The control program further includes a logic engine which applies rules to user entered parameters to determine additional infusion characteristics and to thereby weigh various intravenous devices. Based on the assigned weights, the logic engine returns with a recommended intravenous device which is then displayed by the execution program to the user.

35 Claims, 4 Drawing Sheets

Select an IV Infusion

Step 1: Drug Selection
Category [Antihistamines]   Drug [Benadryl]

Step 2: Dosage Selection
Quantity  Frequency  Duration
[10] [mg]  [q6h]  [1] [Hour]
[Previous]  [Next]

Step 3: Delivery Method
⊙ Continuous
○ Push
○ Piggy Back
Delivery Time [15] [min]

Step 4: Diluent
Mix with
[50] [mL]
[0.9% Sodium Chlor]

Step 5: Patient Condition
Estimated Length of Therapy [1] [Hour]
☐ Hemodynamic Monitoring
Vascular Intergrity [Normal]
Treatment Location [Hospital]

OTHER PUBLICATIONS

Merrill, G.L., et al. "Virtual Reality Debuts in the Teaching Laboratory in Nursing", *Journal of Intravenous Nursing.* vol. 19, No. 4 (Jul./Aug., 1996), pp. 182–187.

Rennels, G. D., et al. "Artificial Intelligence Research in Anesthesia and Intensive Care", *J. Clinical Monitoring.* (Oct., 1988), pp. 274–289.

Ritchey, N.P., et al. "Optimal Interval for Triple–lumen Catheter Canges: A Decision Analysis", *Medical Decision Making.* (Apr.–Jun., 1995), pp. 138–142.

Séné, B., et al. "A General Model of Drug Prescription", *Methods of Information in Medicine.* vol. 34, No. 4 (1995), pp. 310–317.

Shahsavar, N., et al. "Evaluation of a Knowledge–Based Decision–Support System for Ventilator Therapy Management", *Artificial Intelligence in Medicine.* vol. 7 (1995), pp. 37–52.

Silverman, H. *A Digitalis Therapy Advisor.* Howard Silverman: Cambridge Massachusetts. Dec., 1974.

Tsai, C. A. *Treatment Protocols for a Medical Expert System: Solving Problems in Text Delivery and Knowledge Engineering.* Chien–Min A. Tsai: Chicago Illinois. Aug., 1990.

Select an IV Infusion

Step 1: Drug Selection
Category [Antihistamines ▷]   Drug [Benadryl ▷]

Step 2: Dosage Selection
Quantity [10 ▷] mg   Frequency [q6h ▷]   Duration [1] [Hour ▷]

Step 3: Delivery Method
◉ Continuous
○ Push
○ Piggy Back
Delivery Time [15] [min ▷]

Step 4: Diluent
Mix with [50 ▷] mL
[0.9% Sodium Chlor ▷]

[Previous]   [Next]

Step 5: Patient Condition
Estimated Length of Therapy [◁ 1 ▷] [Hour ▷]   ☐ Hemodynamic Monitoring   Vascular Intergrity [Normal ▷]   Treatment Location [Hospital ▷]

FIG-4

SYSTEM AND METHOD FOR SELECTING AN INTRAVENOUS DEVICE

BACKGROUND

1. The Field of the Invention

The invention relates to the field of medical treatment, and is a system and method for recommending an intravenous device for intravenous infusion therapy of a patient.

2. The Background Art

Intravenous infusion therapy is often used to administer medications or other intravenous fluids, collectively referred to herein as infusions, directly into the circulatory system of a patient. Intravenous devices are used in intravenous infusion therapy for insertion into the patient's body to provide a means of delivery of the infusion. Intravenous devices may also be used to administer blood and blood products, nutrition solutions, and even for blood withdrawal for testing.

When the infusion involves a medication it is typically composed of a prescribed drug and in some cases a diluent. The infusion is placed in a container such as a bag, bottle, or syringe and is hung from a rack above the patient. In one approach, gravity dictates the flow of the infusion to the patient. In this method, a tube leads from the container to an intravenous device which is inserted into a peripheral vein or into another area of the patient's body. Alternatively, an infusion pump may be employed to provide a steady prescribed flow or push of the infusion to the patient. With this method, the tube leads from the container to an infusion pump. The infusion pump provides a user interface to allow control of the flow of the infusion into the patient. The infusion pump is equipped with an output tube which leads to an intravenous device which is inserted into the patient.

Several different intravenous devices exist for insertion into the peripheral veins of a patient to thereby provide delivery of an infusion. Common intravenous devices include infusion needles which are used for single dose administrations into the small peripheral vein in the lower arms or hands.

Other intravenous devices are designed for administrations of multiple doses and include winged infusion needles, peripheral intravenous catheters, midline catheters, peripherally inserted central catheters (PICC), and surgically placed catheters or ports. Peripheral intravenous catheters and winged infusion needles are inserted into a small peripheral vein in the lower arms and hands. With peripheral intravenous catheters, the entry site must be changed every few days or as required. The peripheral intravenous catheter is often used for short-term therapy or it may be used until a long-term access device can be inserted.

A midline catheter is an intravenous catheter inserted in the anticubital area of the arm. The midline catheter may be up to eight inches in length. With proper care a midline catheter may be left in place from 2 to 6 weeks or longer. Accordingly, midline catheters are typically used for intermediate term therapies.

A PICC is a long catheter composed of a soft material which is inserted in the anticubital area of the arm and threaded into the superior vena cava above the right atrium. The PICC may be up to 25 inches in length and is threaded along the course of the veins to a location deep in the large veins of the chest. PICCs are a very special type of intravenous catheter and a chest X-ray is usually done to confirm that the PICC is in the correct location. With proper care a PICC may be left in place for 6 months or as long as the therapy may be prescribed. Hence, PICC catheters are ideally suited for long term therapy.

Surgically placed catheters or ports are inserted under the skin in the upper chest area. These intravenous devices are threaded through the major neck vein such as the subclavian vein and into a larger chest vein such as the superior vena cava. The tip of these intravenous devices may rest in the atrium of the heart. These devices are intended for long term therapy and need removal only if complications arise.

Selection of an appropriate intravenous device requires careful consideration to ensure that the infusion is properly administered. Some factors in selecting an appropriate intravenous devices include the drug and the diluent in the infusion, the dosage of the infusion, the length of the therapy, the evasiveness of the intravenous device, the dwell time of the intravenous device in the body, and the vascular integrity of the patient's peripheral veins. The patient's vascular integrity will effect how the veins are accessed and how much pressure is applied to the veins. The intravenous device must also provide a proper dose rate and an equal distribution of the infusion over time. For example, some infusions are administered in a bolus dose for quicker absorption while other infusions will have smaller doses for slower absorption by the patient. A patient may be unduly harmed or the effectiveness of the infusion treatment may be compromised by an inappropriate intravenous device.

With the exception of surgically placed catheters, the infusion is often administered to the patient by a clinician other than the physician. Often times the clinician administering the drug is not an infusion expert and has limited experience in the field. The clinician must have adequate knowledge regarding the operation and application of different types of intravenous devices available. Clinicians administrating intravenous devices must also be aware of the advances and developments in intravenous devices. Because of financial constraints, medical facilities are not always able to staff clinicians who are expert in infusion therapy. Recent trends in the medical field indicate a reduced number of intravenous infusion therapy experts. With the various intravenous devices available and numerous potential complications, selection of an intravenous device for treatment is confusing and complex to the un-experienced clinician.

In selecting the appropriate intravenous device, the clinician is advised to perform a series of computations to determine the characteristics of the infusion. Such computations are time consuming and subject to human error. Furthermore, clinicians with inadequate experience or training will be unable to properly perform the computations. The clinician must also choose an intravenous device based on the physical characteristics of the patient, the delivery method, and therapy length. These and other factors must be carefully considered and weighed against one another in order to select an appropriate device. Such a decision can be confusing and ambiguous to the untrained clinician. Ideally, selection is made based on the advice of an infusion therapy expert. However, as mentioned previously, infusion therapy experts are not always present and this can result in inappropriate selection of an intravenous device.

Computer systems have been successfully incorporated into a variety of applications, such as agriculture, chemistry, engineering, finance, management, health care, manufacturing and others. In the field of health care, hospitals and medical laboratories have used computers to analyze blood and run certain tests. Computer systems have also been established for recommending drug therapies for certain types of cancers. Other computer systems have been established for recommending therapeutic drugs for nervous system disorders. Some computer systems have been designed for recommending treatment of more specific disorders such as breast cancer and hepatitis. Still other computer systems have addressed treatments in the fields of epilepsy, poison control, childbirth, and physical rehabilitation.

Although the previous computer systems have been designed to address a relatively wide range of health care concerns, little has been done in the area of intravenous infusion therapy. None of the previously mentioned computer systems designed for health care applications have provided the ability to assist a clinician in the selection of an intravenous device.

From the foregoing it will be appreciated that it would be an advancement in the art to provide a computer system and method to aid a clinician in recommending an intravenous device for intravenous infusion therapy.

It would be a further advancement in the art to provide a computer system and method which bases its recommendation of an intravenous device on the physical characteristics of the infusion and the patient as entered by the clinician.

It would be another advancement in the art to provide a computer system and method for recommending an intravenous device which is simple to understand and operate.

It would be yet another advancement in the art to provide a computer system and method for recommending an intravenous device which may be updated to keep pace with advances in intravenous infusion therapy.

Such a device is disclosed herein.

BRIEF SUMMARY

The invention provides a computer system which recommends an intravenous device to a clinician based on input entered by a user regarding the infusion and the patient's physical characteristics. The computer system comprises a processor, a memory, and a control program stored in the memory which directs the processor in performing the functions of the invention. The control program includes an execution program for interacting with the user to elicit responses and to provide output to the user. The execution program is designed to be user-friendly and easily operated by unsophisticated personnel. A user inputs parameters to the prompts of the execution program to provide the control program with information regarding the infusion, the vascular integrity of the patient, and the delivery method. The user entered parameters are stored in a memory for subsequent computation.

The control program computes the physical characteristics of the infusion, such as the osmolality, and then proceeds with a series of tests for weighing various intravenous devices. Each test weights each intravenous device based on rules relating to the infusion, patient vascular integrity, and the nature of the infusion therapy. Each test then assigns a weight value to each intravenous device. Weight values for each intravenous device are totaled and reviewed by the control program in order to select an intravenous device. The control program returns with a recommended intravenous device which is then displayed by the execution program to the user.

Thus, it is an object of the invention to provide a system which recommends an intravenous device for infusion therapy based on expert knowledge and which eliminates the need for the clinician to perform tedious computations.

These advantages of the present invention will become more fully apparent by examination of the following description of the preferred embodiments and the accompanying drawings.

BRIEF DESCRIPTION OF THE DRAWINGS

In order that the manner in which the above-recited and other advantages and features of the invention are obtained, a more particular description of the invention summarized above will be rendered by reference to the appended drawings. Understanding that these drawings only provide selected embodiments of the invention and are no, therefore to be considered limiting of its scope, the invention will be described and explained with additional specificity and detail through the use of the accompanying drawings in which.

DETAILED DESCRIPTION OF THE PREFERRED EMBODIMENTS

Figure 1:
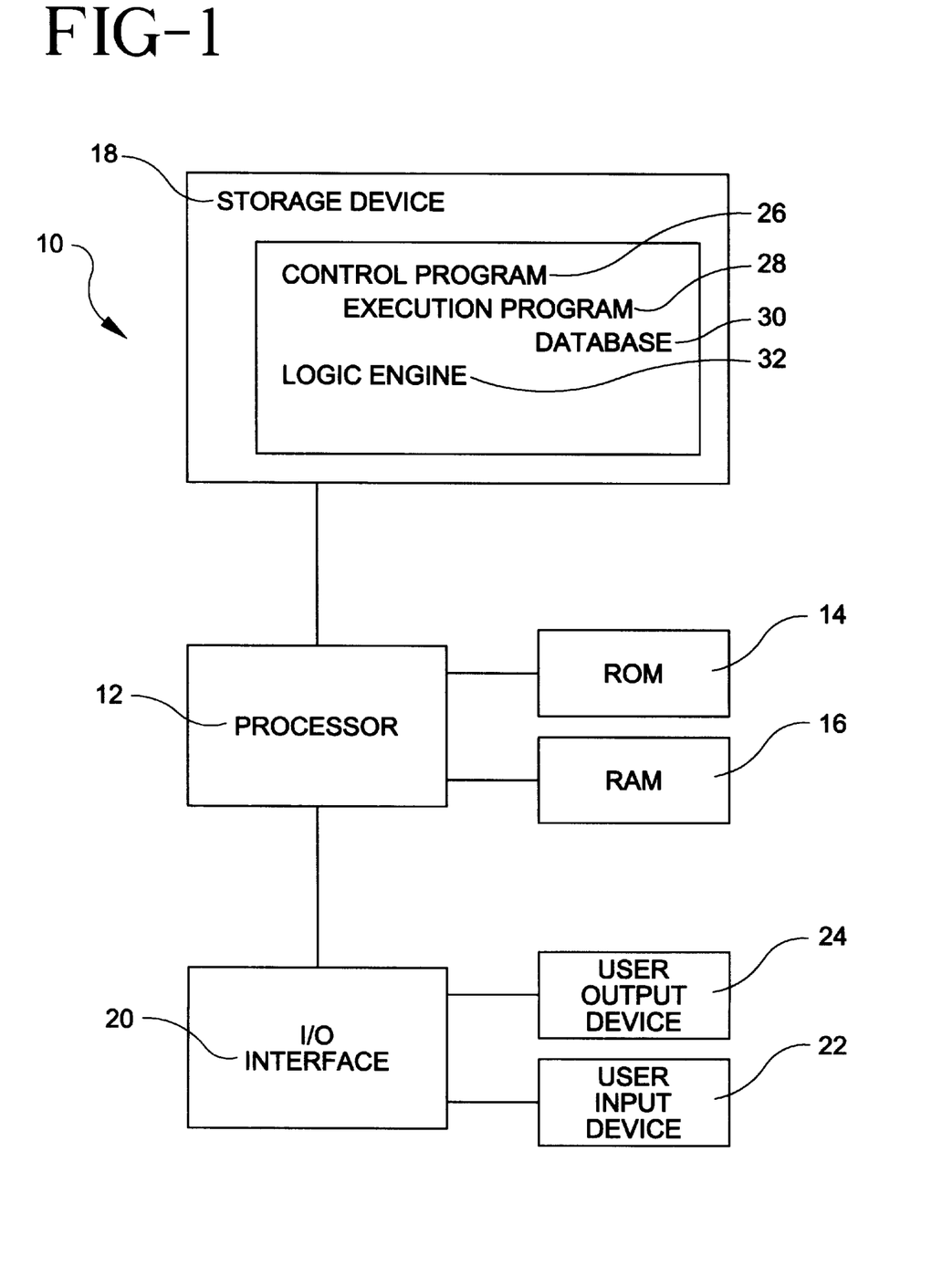
FIG. 1 illustrates one presently preferred embodiment of the computer system of the present invention.

Reference is now made to the embodiments and methods illustrated in FIGS. 1 through 4. With reference to FIG. 1 there is generally designated the computer system 10 of the present invention. The computer system 10 comprises a conventional processor 12 with sufficient capacity to perform the functions of the system. The processor 12 is in electrical communication with a read only memory 14 (ROM) which provides initial configuration and verification of the computer system 10 upon start up of the system. The processor 12 is further in electrical communication with a random access memory (RAM) 16 which provides short term storage of data and programming for the processor 12. The processor 12, the ROM 14, and the RAM 16 are defined herein as the central processing unit of the computer system 10.

The computer system 10 also comprises a storage device 18 which is a computer usable medium with long term memory storage capability. In one presently preferred embodiment, the storage device 18 comprises a nonvolatile memory. Alternatively, the storage device 18 may be embodied as a floppy disk with a corresponding floppy disk drive or as a compact disk with a corresponding compact disk drive. In all of the embodiments, the storage device 18 is in electrical communication with and accessible by the processor 12.

The computer system 10 further comprises a conventional input/output interface 20 which is in electrical communication with the processor 12. The input/output interface 20 controls the flow of data to and from devices which are external to the central processing unit such as those providing interactive interface with a user. A user input device 22 is in electrical communication with the input/output interface 20 and enables the user to input commands to the processor 12. The user input device 22 may be embodied as a keyboard, mouse, voice recognition processors or other such conventionally known input devices. A user output device 24 is also in electrical communication with the input/output interface 20 and enables the computer system 10 to display and prompt for input, display results, and display the status of the computer system. In one embodiment, the user output device 24 may be embodied as a conventional cathode ray tube (CRT) screen.

In one presently preferred embodiment, the user input device 22 and the user output device 24 are jointly embodied as a touch screen CRT. The torch screen CRT displays output to the user and conveys input to the processor by the user contacting the appropriate locations on the screen. In such an embodiment, the user input device 22 may also comprise other input devices such as a keyboard and mouse.

The computer system 10 further comprises a control program 26 which is embodied as computer readable code and directs the processor 12 in performing the functions of the invention. In one presently preferred embodiment, the control program 26 is preferably stored in a computer-usable medium such as the storage device 18 as shown in FIG. 1. In another alternative embodiment, the control program 26 is stored in an integrated memory circuit which is in electrical communication with the process 12. In yet another embodiment, the control program 26 is partially stored in the ROM 14 and partially stored on the above mentioned storage device 18. In such an embodiment, the processor 12 initially accesses the ROM 14 upon start up of the system. The control program 26 begins verification and configuration of the other storage devices to locate the remainder of the control program 26. The processor 12 is then directed to the appropriate storage device to retrieve the remainder of the control program 26.

The control program 26 encompasses all the software programming necessary to perform the function of the invention and comprises an execution program 28, a logic engine 30, and a database 32. Control of the system is transferred primarily between the execution program 28 and the logic engine 30 in performing the function, of the invention.

The execution program 28 commences operation of the system and provides the interface with the user. The execution program 28 prompts the user for all inputs including, at a minimum, the physical properties of the infusion, the delivery method, and the vascular integrity of the patient. The user responds to these prompts by entering inputs in the form of parameters defined by the execution program 28. This provides a basis from which the control program 26 may determine the necessary physical characteristics of the infusion. The execution program 28 assembles the user entered parameters into data files which are preferably stored in the RAM 16 for speedy access by the processor 12. The data files are specific to each patient and infusion and therefore must be created with each use of the computer system 10. Once the system has determined a recommended intravenous device, the execution program 28 displays the recommended intravenous device to the user by means of the user output device 24. The execution program 28 may also display additional information such as a compilation of the user entered parameters and characteristics about the infusion calculated by the system.

The execution program 28 may prompt for input and display output in a variety of formats. In one presently preferred embodiment, the execution program includes a graphical user interface (GUI) to elicit responses to a series of prompts relating to the infusion, the patient's vascular integrity, and the delivery method. The GUI employs suitable text oriented graphics and icons to elicit responses from a user.

The logic engine 30 performs the computations in order to recommend an intravenous device. The logic engine 30 accesses the data files established by the execution program 28 to retrieve the user entered parameters. The logic engine 30 contains rules relating physical characteristics of the infusion and the vascular integrity of the patient to various intravenous devices which are to be considered for selection. The logic engine 30 also includes a database 32 which contains expert information relating to infusion therapy and intravenous devices. The database 32 may be updated periodically in accordance with currently available expert knowledge. The database 32 includes data and rules regarding the physical properties of various drugs and diluents and sufficient information to determine the physical characteristics of infusions composed of the drugs and diluents.

The logic engine 30 accesses the database 32 for the data and rules which are applicable to the user entered parameters. The logic engine 30 first processes the rules which correspond to the physical characteristics of the infusion to produce further information regarding the infusion. The logic engine 30 stores the computed physical characteristics of the infusion in an updated data file. The logic engine 30 then processes the rules which weigh each intravenous device according to the infusion physical characteristics, vascular integrity of the patient, and the delivery method. In one presently preferred embodiment, the rules are formulated so that less preferable devices are assigned greater negative weights. All weights for each intravenous device are then summed to produce a total negative weight value. The intravenous device with the least negative weight value is returned as the recommended intravenous device for the procedure. The rules are designed to balance one another and assign appropriate total negative weight values which result in selection of the most suitable intravenous device.

Figure 2:
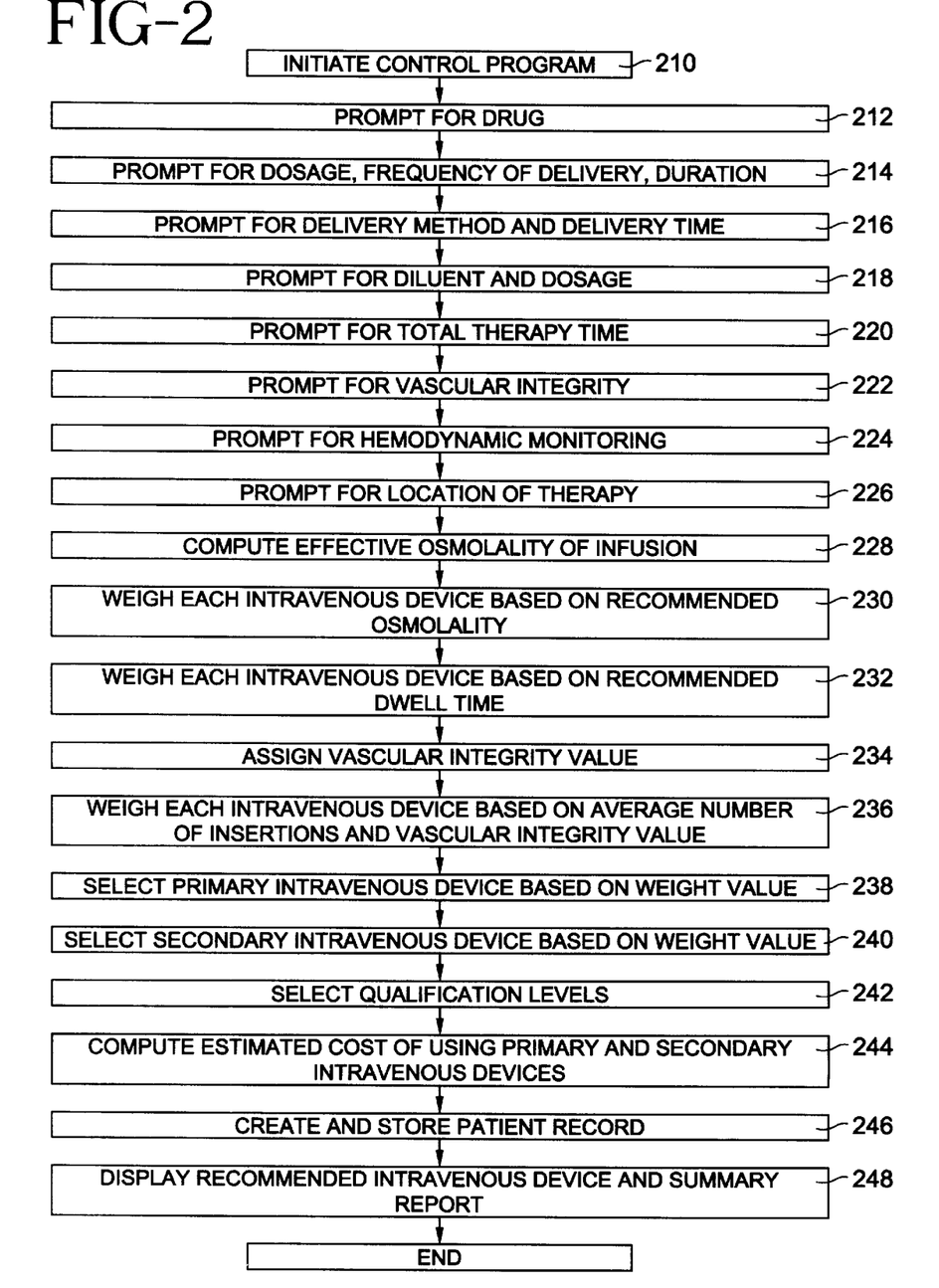
FIG. 2 is a flow diagram of the steps performed by the control program of one presently preferred embodiment of the system.

The operation of the computer system in accordance with the present invention is now described. With reference to FIG. 2, the steps performed by the control program 26 of the invention are generally designated and more specifically by the execution program 28 and logic engine 30. The steps performed by the control program 26 are accomplished through the cooperative interaction of the execution program 28, the logic engine 30, and the database 32. All components of the control program 26 are compatible with and are executed by the processor 12.

In step 210 the control program is initiated by the user invoking the batch file. This may be done by the user entering the typed name of the batch file or selecting an appropriate icon in a GUI environment. Upon execution of the control program 26, the processor 12 accesses the storage device 18 upon which the control program resides. The control program 26 is then loaded into the RAM 16 where it is accessed by the processor 12 throughout operation. The control program 26 then calls the execution program 28 which commences operation in step 212.

Figure 3:
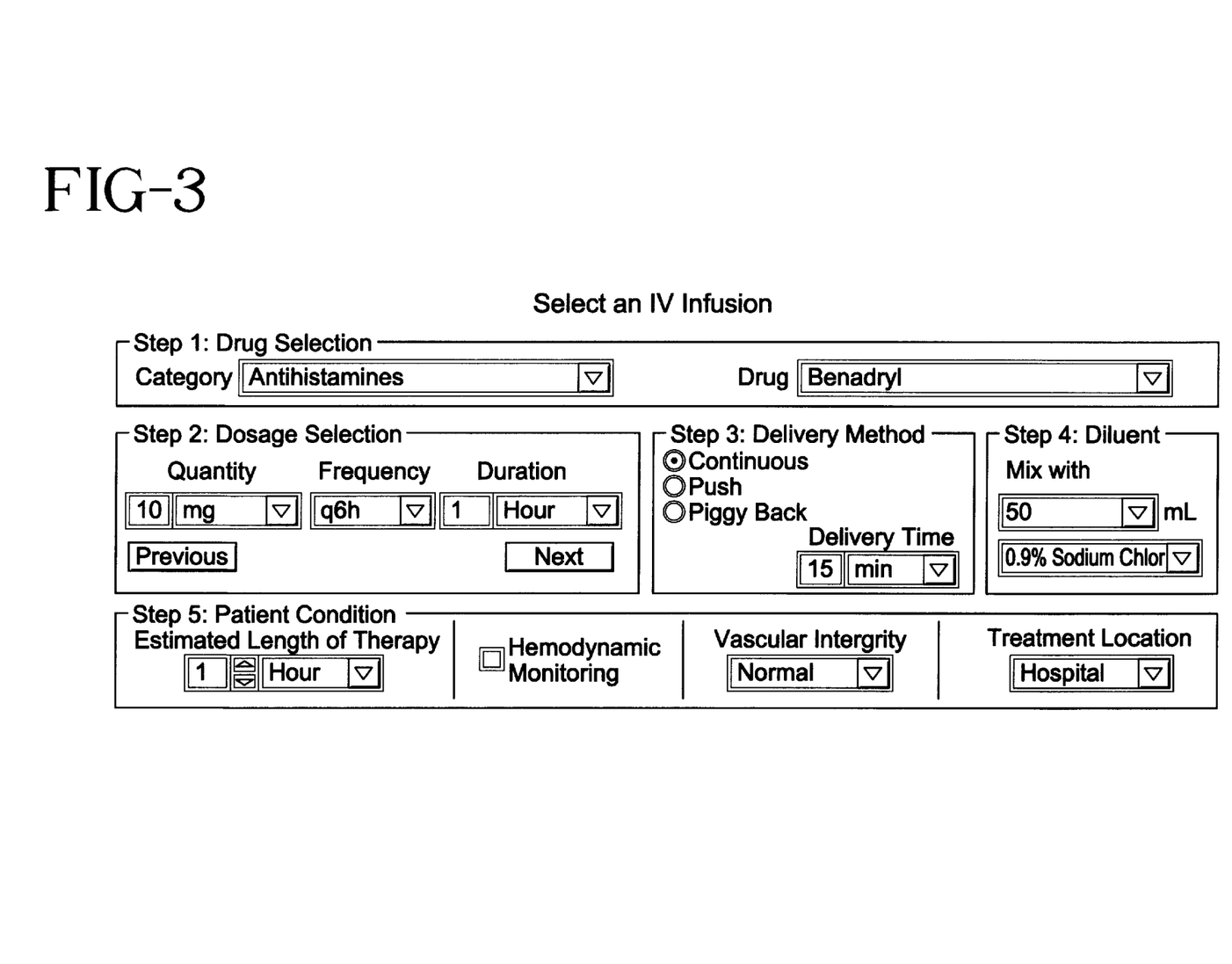
FIG. 3 is one example of screen which may be displayed in order to prompt the user for information concerning characteristics of the infusion, the patient, and the therapy.

In step 212, the execution program 28 begins prompting the user for inputs. First, the execution program 28 prompts the user for the drug to be infused. With reference to FIG. 3, an illustration of one screen that may be displayed to the user is shown wherein a "drop box" for drug selection is displayed. The user clicks on the box to display the drug list and then selects the prescribed drug from a list of drugs. Selection is effected through the user input device 22. In one presently preferred embodiment, as shown in FIG. 3, drugs may be divided according to a category which then effects the drugs available on the drug list. The grouping of the drugs into categories is provided as a convenience to the user to limit the amount of searching through the drug list. Thus, as shown in FIG. 3, there is a drop box for the drug category and one for the list of drugs within the category. In an alternative embodiment, all drugs may be displayed in a single list but this method may be cumbersome to the user. After entry of the drug, the user entered parameter representing the drug is placed in a data file. The execution program 28 then proceeds to step 214.

In step 214, the execution program displays a screen such as that show in FIG. 3 to prompt for the drug dosage, the frequency of delivery, and the duration. The drug dosage is inputted as a quantity such as grams or milliliters. The frequency of the delivery is entered as number of deliveries per hour or day or for a set number of days. The duration is the length of time that the infusions are to be administered. Thus, one example of an input would be 2 grams of a particular drug every other day for ten days, wherein ten days is the duration. Such input is designed to reflect the prescribed infusion therapy.

In step 216, the execution program displays a screen such as that shown in FIG. 3 to prompt for the delivery method. In one presently preferred embodiment, such as that shown in FIG. 3, the delivery methods available for selection are continuous, push, and piggyback. The delivery time for each infusion is also entered but also depends on the delivery method and the volume of the infusion. The delivery time is defined herein as the time to deliver the infusion into the patient's body. The continuous method has a delivery time which corresponds with the volume of the infusion because the infusion is constantly being administered by gravity. The push method has an effectively nonexistent delivery time because the infusion is pushed into the patient by an infusion pump within a relatively short period of time such as a number of seconds. The piggyback method delivers a specific amount of the infusion in conjunction with a first infusion. With the piggyback method, the delivery time thus depends on the delivery method of the first infusion and is either effectively zero, as with the push, or is a duration which corresponds to the first infusion.

In step 218, the execution program displays a screen such as that shown in FIG. 3 to prompt for the type of diluent and the dosage of diluent. The list includes a list of common diluents which are acceptable for infusion therapy such as normal saline, D5W, and sterile water. The dosage is given in a quantity such as grams or milliliters. The user selects the appropriate diluent from the list provided and the user entered parameter is entered into a data file. The amount of diluent used may effect the delivery time prompted for in step 216 because of the increased volume to the infusion. With some infusion therapies, such as many therapies using a push method, there may not be a diluent. In those cases, the diluent entries remain blank.

In step 220, the execution program prompts the user for the estimated length of total infusion therapy time shown in FIG. 3. The total infusion therapy time is the total amount of time that the patient is to remain under infusion time. The total infusion therapy time is at least as long as the duration which was given in step 214 and may be longer if additional infusions are anticipated. The total infusion therapy time may also be equal to the duration time. Often times the total infusion therapy time is a judgment call for the clinician.

In step 222, the execution program prompts the user for the vascular integrity of the patient as shown in FIG. 3. The vascular integrity of a patient is typically categorized as good, normal, normal-bad, and critical.

In step 224, the execution program further prompts the user as to whether there is hemodynamic monitoring of the patient as shown in FIG. 3.

In step 226, the execution program prompts the user as to whether the patient is being treated at a hospital facility or at home as shown in FIG. 3.

All parameters entered by the user are converted by the execution program into data usable by the computer and stored in a temporary data file. The data file is stored in a memory such as the RAM 16. In step 228, the execution program 28 transfers control to the logic engine 30. In step 228, the logic engine 30 computes the osmolality of the entered drug. Osmolalities for numerous drugs are stored in the database 32. Thus, the logic engine 30 first reviews the database 32 to find and retrieve the osmolality value. If the osmolality of the entered drug is not in the database 32 then the logic engine 30 derives the osmolality by a formula which accounts for the number of electrolytes or free ions in the drug. Alternatively, the osmolality may be computed from the molecular weight of the drug. Such equations are commonly known by those of skill in the art. The logic engine 30 further computes the osmolality of the diluent (if applicable) based on the kind of diluent and the amount. The diluent osmolality is usually known and is stored in the database 32.

The logic engine 30 further combines the dosage of the drug and the diluent (if applicable) to derive the dosage of the infusion. The logic engine 30 then computes the effective osmolality of the infusion which is a combination of the drug and the diluent (if applicable). In computing the effective osmolality, the logic engine 30 accounts for the drug osmolality, the diluent osmolality (if applicable), and the volume of the infusion as a whole. Such formulas for computing effective osmolality are commonly known to those of skill in the art. The osmolality effects selection of intravenous devices because the higher the osmolality value, the more toxic the infusion is to the patient. Consequently, more toxic infusions require insertions into larger veins and a suitable intravenous device must be selected.

In an alternative embodiment, the logic engine 30 further computes the ph level of the infusion. This may be accomplished by accessing the database 32 for ph levels of commonly known infusions or computing the ph level based on equations well known to one of skill in the art. In such an embodiment, the ph level of the infusion may effect selection of the type of vein and, consequently, the type of intravenous device.

After entry of the user parameters and computation of the effective osmolality of the infusion, the logic engine 30 begins weighing a series of intravenous devices which are to be considered for selection. The logic engine 30 consists of a series of tests which are performed for weighing each of the intravenous device. Each test has rules which relate the user entered parameters to each intravenous device to produce a weight value. The intravenous devices are considered in their order of evasiveness with the least evasive device considered first. In one presently preferred embodiment, the intravenous devices to be considered by the control program are the following: the peripherally inserted central catheter (PICC) SVC, the PICC midclavicular, the midline catheter, the I.V. catheter, the winged needle set, and surgically placed catheters and ports. In alternative embodiments, additional intravenous devices may also be included and corresponding rules would be included for relating each additional device to the user entered parameters. The control program 26 may be updated as desired to include additional intravenous devices presently available or which are subsequently developed. Accordingly, intravenous devices which are no longer favored may be deleted from the control program 26.

The logic engine 30 proceeds to step 230 which weighs the osmolality for each intravenous device. The logic engine 30 determines if the effective osmolality produced in step 228 exceeds the recommended osmolality for each intravenous device. The recommended osmolality for each intravenous device is retrieved by the logic engine 30 from the database 32. If the effective osmolality exceeds the osmolality for the intravenous device, then that intravenous device is assigned a negative weight value. The assigned negative weight value is retained by that intravenous device for the remainder of the process. In one presently preferred embodiment, the rule for assigning a negative weight value is: [(the difference that the effective osmolality exceeds the recommended osmolality of the intravenous device)/10]*5. One of skill in the art will appreciate that the rule may be adjusted as desired as long as it produces a result which recommends an appropriate intravenous device. In one presently preferred embodiment, the rule balances with other subsequent rules to produce a recommended intravenous device which is in harmony with infusion expert opinion.

The logic engine 30 then proceeds to step 232 which compares an anticipated dwell time for the therapy to the recommended dwell time for each intravenous device. The dwell time is the total length of time that the device remains in the body and each intravenous device is suitable for different dwell times. For example, winged infusion needles and peripheral catheters are generally suitable for short term use of two to three days, midline catheters are suitable for two to four weeks, PICC midcavicular are suitable for two to three months, PICC SVC are suitable for up to one year, and surgically implanted catheters are suitable for indefinite use. Recommended dwell times for each intravenous device are stored in the database 32 and retrieved by the logic engine 32 for comparison. The anticipated dwell time is the length of time that the intravenous device is likely to remain in the patient for the infusion therapy. The anticipated dwell time for the infusion therapy is based on the duration entered in step 214 and the total infusion therapy time entered in step 220. The anticipated dwell time can not be less than the duration and is considered to be less than the total infusion therapy time. Thus, the anticipated dwell time can be a range between the duration and the total infusion therapy time.

In one presently preferred embodiment, the rule used to assign a negative weight value based on dwell time is: number of days that the anticipated dwell time possibly exceeds the recommended dwell time*15. This rule is designed to assign a significant negative weight so that short term intravenous devices are normally eliminated if their recommended dwell time is exceeded. As before, the negative weight value is summed with previous negative weight values for each intravenous device.

The logic engine 30 proceeds to step 234 wherein the patient's vascular integrity is considered. A vascular integrity value is assigned based on the user inputted vascular integrity of the patient. The vascular integrity value increases as the patient's vascular integrity declines from good to critical. In one presently preferred embodiment, the vascular integrity values assigned to good, normal, normal-bad, and critical are 1, 5, 10, and 50 respectfully. The vascular integrity value of the patient is then stored in a data file.

The logic engine 30 next proceeds to step 236 wherein the average number of insertions by each intravenous device for the anticipated dwell time is computed. This computation is derived from average use data which is stored in the database 32 and retrieved by the logic engine. A negative weight value is assigned to each intravenous device which is based on the number of insertions and the vascular integrity value derived in step 234. In one presently preferred embodiment, the equation is: total number of insertions*vascular integrity value. Thus, if a patient has good vascular integrity, each required insertion will result in a negative 5 weight. On the other hand, if a patient has critical vascular integrity each insertion will result in a negative 50 weight. In this manner, intravenous devices which require multiple insertions are likely to be excluded from selection where the patient has poor vascular integrity. The negative weight value computed in step 236 for each intravenous device and is summed with previous negative weight values.

A running total of all negative weight values assigned to each intravenous device is maintained. In this manner the logic engine 30 sequentially applies the rules relating the user entered parameters to the different intravenous devices.

In step 238 the total negative weight value of each intravenous device is reviewed in order to determine selection. The logic engine 30 reviews the intravenous devices in order from least evasive to most evasive and selects the intravenous device which has the lest negative weight. An intravenous device with a zero negative weight score would be considered a perfect match for the patient and the infusion therapy. In the event of two zero negative weight scores, the less evasive device is selected. The selected device is the primary device for the infusion therapy.

The logic engine 30 always selects one of the available intravenous devices. In the event that all intravenous devices have unacceptably high negative weight scores then the logic engine 30 has a default selection. In one presently preferred embodiment, the default selection is the Acute CVC device. Thus, in one presently preferred embodiment, the intravenous device is selected from the group of PICC SVC, PICC midclavicular, midline catheter, I.V. catheter, winged needle set, and surgically placed catheters and ports with a default selection of the Acute CVC.

In step 240, the logic engine 30 eliminates the selected primary intravenous device from consideration and then reviews the total negative weight values of each intravenous device to select a secondary device. In this manner, a secondary device is always selected in the event that the primary device is unavailable or a qualified clinician is unavailable to administer the primary device. If no secondary device has an acceptable negative weight value, then the logic engine 30 selects the default of the Acute CVC device.

In step 242, the logic engine 30 selects the qualification level of the clinician who is to administer the primary device and the secondary devices. Information relating intravenous devices to qualification levels is retained in the database 32. The logic engine 30 retrieves the qualification level for the primary and secondary intravenous devices.

In step 244, the logic engine 30 estimates the cost of using the primary device and the secondary device in the infusion therapy. The cost of using the primary device and the secondary device is computed by using known estimates which are stored in the database 32 and retrieved by the logic engine 30. Such cost estimates include the cost to administer the devices and can include the hourly rate of the clinician. The cost is also based on user entered parameters such as the dwell time, the length of the infusion therapy, the average number of insertions, costs for parts of the intravenous device, and whether it is administered in a hospital, outpatient facility, or at home. The database 32 may be updated periodically to reflect economic changes to produce a more accurate cost estimate.

In an alternative embodiment, the estimated cost of each intravenous device is derived and used to assign negative weight values to each intravenous device prior to selection of an intravenous device. In this manner, the total negative weight value for each intravenous device is influenced and selection of recommended intravenous devices are based in part on the estimated cost.

In step 246, the logic engine 30 compiles the user entered parameters, the selected primary and secondary devices, and other computations relating to the primary and secondary devices and saves it as a patient record. The patient record is preferably stored on the storage device 18 of the computer system. The patient record is stored for later retrieval to review the results of the infusion therapy in comparison to that estimated by the control program 26.

Figure 4:
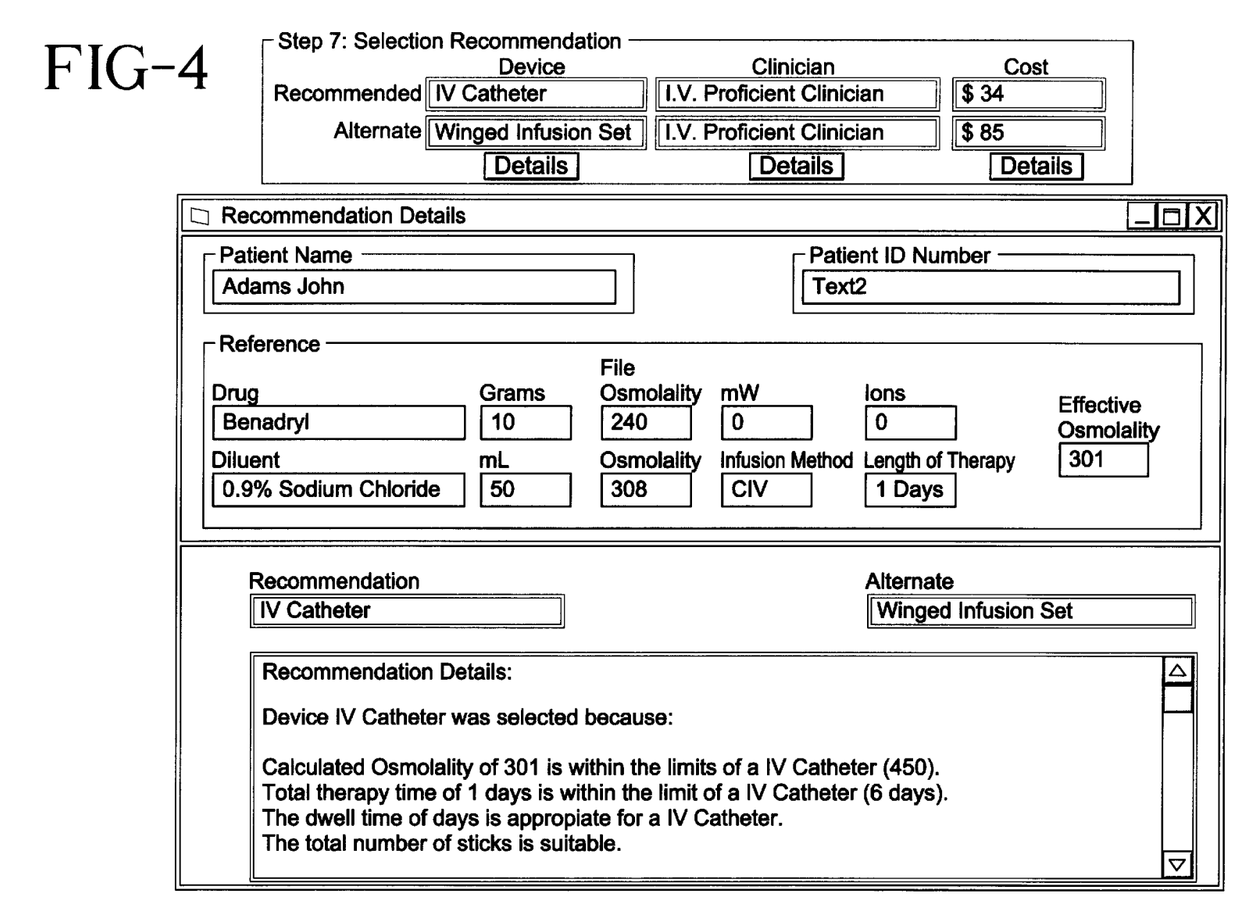
FIG. 4 illustrates an example of a screen which may be displayed to inform the user of the results.

In step 248, control is transferred to the execution program 28 which produces a display of the computations performed by the control program 26 on the user output device 24 as shown in FIG. 4. The execution program 28 displays the primary device, the secondary device, and a summary report which includes a compilation of the user entered parameters and computed osmolality of the infusion. The summary report further includes reasoning or logic in human readable form which justifies selection of the primary device. The summary report also provides the qualification level of the clinician administrating the infusion and an estimate of the cost of using the primary device. The summary report is provided to allow a user to easily and quickly view the results and evaluate whether the primary device or the secondary device is acceptable for the infusion therapy. One of skill in the art will appreciate that the output screen shown in FIG. 4 is illustrative only and may be displayed in numerous ways without departing from the scope of the invention. For example, the information displayed in the output screens may be further separated into multiple screens.

The control program 26 of the invention allows the user to manipulate the user entered parameters until an acceptable intravenous device is selected. Thus, a user may alter the infusion therapy and reenter the user parameters until an intravenous device with an acceptably low negative weight value is accepted. In practice, the intravenous devices have computed total negative weights which distribute into an inverse bell curve. The pinnacle of the inverse bell curve is the intravenous device which the logic engine 30 selects.

One of skill in the art will appreciate that the steps performed by the control program need not be necessarily performed in the sequence illustrated. The control program is capable of performing the functions of the invention using a variety of different steps in different sequences. For example, the steps 230 through 236 may be performed in a different order as long as a running total of the negative weight values is maintained. Furthermore, the order in which user inputs are entered may be altered.

One of skill in the art will appreciate that there are numerous embodiments for weighing different intravenous devices based on user entered parameters and rules relating the parameters to each intravenous device. It should be appreciated that the system and methods of the present invention are capable of being incorporated in the form of a variety of embodiments, only a few of which have been illustrated and described above. Those illustrated in one presently preferred embodiment are to be considered in all respects only as illustrative and not restrictive of the scope of the invention. The purpose of the invention is to weigh the intravenous devices and balance those weights with each other in order to consistently select an intravenous device under a variety of circumstances which is in harmony with expert opinion. The rules outlined in one presently preferred embodiment are illustrative of how the user entered parameters may be balanced in order to properly weigh the intravenous devices.

In one alternative embodiment, the logic engine 30 may compute and assign positive weight values for each intravenous device. Positive weights may be assigned for low number of insertions, reduced dwell time, and so forth. However, in this embodiment positive weights are not considered for selecting an intravenous device. Exclusive consideration for selection of an intravenous device rests with the total negative weight values which are computed as explained above. In yet another alternative embodiment, the logic engine 30 may also consider positive points which would offset the total negative weight value of an intravenous device.

In yet an alternative embodiment, the control program 26 may accommodate the entry of two or more drugs that a patient is to take over the course of the infusion therapy. The drugs may be administered in combination or may be administered sequentially. In such an embodiment, the infusion is defined as the plurality of drugs taken either in combination or sequentially. These drugs are entered individually by the user as are their individual dosages. If the drugs are taken in combination, then the frequency of delivery and the duration for the entire infusion is entered. If the drugs are taken sequentially, then the frequency of delivery for each drug is entered and the duration is entered for the entire length of treatment.

The logic engine 30 operates generally as before with the primary difference being in the computation of the effective osmolality in step 228. In step 228, the logic engine 30 computes the osmolality of each drug based on the characteristics of the drug and the volume. If the drugs are taken in combination, then the logic engine 30 computes the effective osmolality of the combination of the drugs. The effective osmolality is then used for subsequent computations. If the drugs are taken sequentially, then the logic engine 30 compares the osmolality of each drug and uses the highest osmolality for subsequent computations. Each drug with their respective osmolality values are displayed to the user in step 248.

As explained herein, the invention aids a clinician by recommending an intravenous device for infusion therapy based on entered physical characteristics of the infusion and the patient. The system selects a recommended device by sequentially applying rules which weigh each intravenous device. Selection is then based on a review of the total weight value assigned to each intravenous device. The user interface allows for easy operation of the system and eliminates the need for a clinician to perform computations necessary for competent selection of an intravenous device. The system may be updated to keep pace with expert knowledge and advances in intravenous infusion therapy.

What is claimed is:

1. A system for providing a user with a recommended intravenous device for delivery of an infusion into a patient based on user entered parameters, comprising:

a computer device having a processor a processor and a memory;

an input interface in electrical communication with the computer device for permitting a user to enter desired parameters;

an output interface in electrical communication with the computer device for providing information from the system to the user; and a control program, stored in the computer device and for execution of the processor, the control program interactively displaying a series of prompts on the output interface to elicit responses from the user concerning the infusion characteristics, wherein the control program stores user entered parameters in the memory, wherein the control program applies rules for computing values for each of a plurality of intravenous devices in accordance with the user entered parameters and for comparing the values to thereby select the most favorable intravenous device, and wherein the control program displays the selected intravenous device to the user on the output interface.

2. The system of claim 1 wherein the control program computes the osmolality of the infusion based on the user entered parameters relating to the physical characteristics of the infusion and wherein the control program computes a value for each intravenous device based on the osmolality of the infusion.

3. The system of claim 1 wherein the control program displays a prompt to elicit a response from the user concerning the vascular integrity of the patient, wherein the control program stores user entered parameters in the memory relating to vascular integrity of the patient, wherein the control program computes the average number of insertions of each intravenous device, and wherein the control program computes a value for each intravenous device based on the vascular integrity of the patient and the average number of insertions.

4. The system of claim 1 wherein the control program displays a prompt to elicit a response from the user concerning the duration of the therapy, wherein the control program stores user entered parameters relating to the duration of the therapy in the memory, and wherein the control program computes a value for each intravenous device based on the duration of therapy and recommended dwell times for each intravenous device.

5. The system of claim 1 wherein the control program recommends a qualification level of a clinician corresponding to the recommended intravenous device and wherein the control program displays the qualification level to the user.

6. The system of claim 1 wherein the control program computes an estimated cost for using the recommended intravenous device and wherein the control program displays the cost to the user.

7. The system of claim 1 wherein the recommended intravenous device is selected from the group consisting of peripherally inserted central catheter, midline catheter, intravenous catheter, winged needle set, and surgically placed catheters catheter.

8. The system of claim 1 wherein the control program creates a patient record which includes the user entered parameters and the recommended intravenous device and wherein the control program stores the patient record in the memory for subsequent retrieval by the user.

9. A computer-usable medium having a computer readable program code embodied therein which causes a computer system to recommend an intravenous device for delivery of an infusion into a patient based on user entered parameters by performing the steps of:

prompting for parameters from the user relating to characteristics of the infusion;

storing user entered parameters in a memory;

applying rules to each of a plurality of intravenous devices in accordance with the user entered parameters to thereby assign each intravenous device a weight value;

comparing the weight value of each intravenous device;

selecting the intravenous device with the most favorable weight value; and displaying the recommended device to the user.

10. The computer-usable medium having a computer readable code of claim 9 which causes a computer system to further perform the steps of:

computing the osmolality of the infusion based on the user entered parameters relating to the physical characteristics of the infusion; and computing a weight value for each intravenous device based on the osmolality of the infusion.

11. The computer-usable medium having a computer readable code of claim 9 which causes a computer system to further perform the steps of:

eliciting a response from the user concerning the vascular integrity of the patient;

storing user entered parameters in the memory relating to vascular integrity of the patient;

computing the average number of insertions of each intravenous device; and computing a weight value for each intravenous device based on the vascular integrity of the patient and the average number of insertions.

12. The computer-usable medium having a computer readable code of claim 9 which causes a computer system to further perform the steps of:

eliciting a response from the user concerning the duration of the therapy;

storing user entered parameter relating to the duration of the therapy in the memory; and computing a weight value for each intravenous device based on the duration of therapy and recommended dwell times for each intravenous device.

13. The computer-usable medium having a computer readable code of claim 9 which causes a computer system to further perform the steps of:

recommending a qualification level of a clinician corresponding to the recommended intravenous device; and displaying the qualification level to the user.

14. The computer-usable medium having a computer readable code of claim 9 which causes a computer system to further perform the steps of:

computing an estimated cost for using the recommended intravenous device; and displaying the cost to the user.

15. The computer-usable medium having a computer readable code of claim 9 which causes a computer system to recommend an intravenous device selected from the group consisting of peripherally inserted central catheter, midline catheter, intravenous catheter, winged needle set, and surgically placed catheters catheter.

16. The computer-usable medium having a computer readable code of claim 9 which causes a computer system to further perform the steps of:

creating a patient record which includes the user entered parameters and the recommended intravenous device; and storing the patient record in the memory for subsequent retrieval by the user.

17. A computer program product for assisting a user, the computer program product comprising:

a computer usable medium having a computer readable program code embodied in the computer usable medium for causing a computer system to recommend an intravenous device for delivery of an infusion into a patient based on user entered parameters, the computer program product having:

computer readable program code for causing the computer system to prompt for parameters from the user relating to characteristics of the infusion;

computer readable program code for causing the computer system to store the user entered parameters in a memory;

computer readable program code for causing the computer system to apply rules to each of a plurality of intravenous devices in accordance with the user entered parameters to thereby assign each intravenous device a weight value;

computer readable program code for causing the computer system to compare the weight value of each intravenous device;

computer readable program code for causing the computer system to select the intravenous device with the most favorable weight value; and computer readable program code for causing the computer system to display the recommended device to the user.

18. The computer program product of claim 17 further comprising:

computer readable program code for causing the computer system to compute the osmolality of the infusion based on the user entered parameters relating to the physical characteristics of the infusion; and computer readable program code for causing the computer to compute a weight value for each intravenous device based on the osmolality of the infusion.

19. The computer program product of claim 17 further comprising:

computer readable program code for causing the computer system to elicit a response from the user concerning the vascular integrity of the patient;

computer readable program code for causing the computer system to store the user entered parameters in the memory relating to vascular integrity of the patient;

computer readable program code for causing the computer system to compute the average number of insertions of each intravenous device; and computer readable program code for causing the computer system to compute a weight value for each intravenous device based on the vascular integrity of the patient and the average number of insertions.

20. The computer program product of claim 17 further comprising:

computer readable program code for causing the computer system to elicit a response from the user concerning the duration of the therapy;

computer readable program code for causing a computer system to store user entered parameters relating to the duration of the therapy in the memory; and computer readable program code for causing a computer system to compute a value for each intravenous device based on the duration of therapy and recommended dwell times for each intravenous device.

21. The computer program product of claim 17 further comprising:

computer readable program code for causing a computer system to recommend a qualification level of a clinician corresponding to the recommended intravenous device; and computer readable program code for causing a computer system to display the qualification level to the user.

22. The computer program product of claim 17 further comprising:

computer readable program code for causing a computer system to compute an estimated cost for using the recommended intravenous device; and computer readable program code for causing a computer system to display the cost to the user.

23. The computer program product of claim 17 further comprising:

computer readable program code for causing a computer system to create a patient record comprising the user entered parameters and the recommended intravenous device; and computer readable program code for causing a computer system to store the patient record in the memory for subsequent retrieval by the user.

24. A system for providing a user with a recommended intravenous device for delivery of an infusion into a patient based on user entered parameters, comprising:

a computer device having a processor and a memory;

an input interface in electrical communication with the computer device for permitting a user to enter desired parameters;

an output interface in electrical communication with the computer device for providing information from the system to the user; and a control program, stored in the computer device and for execution of the processor, the control program interactively displaying a series of prompts on the output interface to elicit responses from the user concerning the infusion characteristics, wherein the control program (i) stores user entered parameters in the memory, to thereby select the most favorable intravenous device, and wherein the control program displays the selected intravenous device to the user on the output interface, (ii) computes the osmolality of the infusion based on the user entered parameters relating to the physical characteristics of the infusion, (iii) computes a first value for each intravenous device based on the osmolality of the infusion, (iv) displays a prompt to elicit a response from the user concerning the vascular integrity of the patient, (v) stores user entered parameters in the memory relating to vascular integrity of the patient, (vi) computes the average number of insertions of each intravenous device, (vii) computes a second value for each intravenous device based on the vascular integrity of the patient and the average number of insertions, (viii) displays a prompt to elicit a response from the user concerning the duration of the therapy, (ix) stores user entered parameters relating to the duration of the therapy in the memory, (x) computes a third value for each intravenous device based the duration of therapy and recommended dwell times for each intravenous device, (xi) sums the first value, the second value and the third value for each intravenous device to calculate a total value, and (xii) compares the total value for each intravenous device.

25. The system of claim 24 wherein the first value is calculated by dividing the difference between the osmolality of the infusion and the recommended osmolality of each intravenous device by ten.

26. The system of claim 24 wherein the second value is calculated by multiplying the average number of insertions by a vascular integrity value.

27. The system of claim 24 wherein the third value is calculated by multiplying the difference between the duration of the therapy and the recommended dwell times by 15.

28. A computer-user medium having a computer readable program code embodied therein which causes a computer system to recommend an intravenous device for delivery of an infusion into a patient based on user entered parameters by performing the steps of:

prompting for parameters from the user relating to characteristics of the infusion;

storing user entered parameters in a memory;

computing the osmolality of the infusion based on the user entered parameters relating to the physical characteristics of the infusion;

computing a first weight value for each intravenous device based on the osmolality of the infusion;

eliciting a response from the user concerning the vascular integrity of the patient;

storing user entered parameters in the memory relating to vascular integrity of the patient;

computing the average number of insertions of each intravenous device;

computing a second weight value for each intravenous device based on the vascular integrity of the patient and the average number of insertions;

eliciting a response from the user concerning the duration of the therapy;

storing user entered parameters relating to the duration of the therapy in the memory;

computing a third weight value for each intravenous device based on the duration of therapy and recommended dwell times for each intravenous device;

computing the sum of the first weight value, the second weight value and the third weight value to calculate a total weight value;

comparing the total weight value for each intravenous device;

selecting the intravenous device with the most favorable weight value; and displaying the recommended device to the user.

29. The system of claim 28 wherein the first weight value is calculated by dividing the difference between the osmolality of the infusion and the recommended osmolality of each intravenous device by ten.

30. The system of claim 28 wherein the second weight value is calculated by multiplying the average number of insertions by a vascular integrity value.

31. The system of claim 28 wherein the third weight value is calculated by multiplying the difference between the duration of the therapy and the recommended dwell times by 15.

32. A computer program product for assisting a user, the computer program product comprising:

a computer usable medium having a computer readable program code embodied in the computer usable medium for causing a computer system to recommend an intravenous device for delivery of an infusion into a patient based on user entered parameters, the computer program product having:

computer readable program code for causing the computer system to prompt for parameters from the user relating to characteristics of infusion;

computer readable program code for causing the computer system to store the user entered parameters in a memory;

computer readable program code for causing the computer system to compute the osmolality of the infusion based on the user entered parameters relating to the physical characteristics of the infusion;

computer readable program code for causing the computer to compute a first weight value for each intravenous device based on the osmolality of the infusion;

computer readable program code for causing the computer system to elicit a response from the user concerning the vascular integrity of the patient;

computer readable program code for causing the computer system to store the user entered parameters in the memory relating to vascular integrity of the patient;

computer readable program code for causing the computer system to compute the average number of insertions of each intravenous device;

computer readable program code for causing the computer system to compute a second weight value for each intravenous device based on the vascular integrity of the patient and the average number of insertions;

computer readable program code for causing the computer system to elicit a response from the user concerning the duration of the therapy;

computer readable program code for causing a computer system to store user entered parameters relating to the duration of the therapy in the memory;

computer readable program code for causing a computer system to compute a third weight value for each intravenous device based on the duration of therapy and recommended dwell times for each intravenous device;

computer readable program code for causing the computer system to select the intravenous device with the most favorable weight value; and computer readable program code for causing the computer system to display the recommended device to the user.

33. The system of claim 32 wherein the first weight value is calculated by dividing the difference between the osmolality of the infusion and the recommended osmolality of each intravenous device by ten.

34. The system of claim 32 wherein the second weight value is calculated by multiplying the average number of insertions by a vascular integrity value.

35. The system of claim 32 wherein the third weight value is calculated by multiplying the difference between the duration of the therapy and the recommended dwell times by 15.

* * * * *